United States Patent [19]

Vonk

[11] Patent Number: 5,185,127
[45] Date of Patent: Feb. 9, 1993

[54] TEST DEVICE INCLUDING FLOW CONTROL MEANS

[75] Inventor: Glenn P. Vonk, Fuquay-Varina, N.C.

[73] Assignee: Becton, Dickinson and Company, Franklin Lakes, N.J.

[21] Appl. No.: 856,885

[22] Filed: Mar. 24, 1992

Related U.S. Application Data

[63] Continuation of Ser. No. 410,372, Sep. 21, 1989, abandoned.

[51] Int. Cl.⁵ .......................................... G01N 33/546
[52] U.S. Cl. ...................................... 422/56; 422/57; 422/58; 422/61; 422/101; 436/531
[58] Field of Search ................... 435/7.8, 7.92, 7.94; 422/56-58, 61, 101; 436/170, 531, 807

[56] References Cited

U.S. PATENT DOCUMENTS

| | | | |
|---|---|---|---|
| 3,888,629 | 6/1975 | Bagshawe . | |
| 4,111,754 | 9/1978 | Park | 422/99 X |
| 4,246,339 | 1/1981 | Cole et al. | 422/101 X |
| 4,277,560 | 7/1981 | Gray et al. | 422/81 X |
| 4,366,241 | 12/1982 | Tom et al. | 422/56 X |
| 4,632,901 | 12/1986 | Valkirs et al. | 422/56 X |
| 4,818,677 | 4/1989 | Hay-Kaufman et al. | 422/56 X |
| 4,916,056 | 4/1990 | Brown, III et al. | 422/56 X |
| 4,920,046 | 4/1990 | McFarland et al. | 422/56 X |

OTHER PUBLICATIONS

Leary, et al. *Proc. Natl. Acad. Sci. USA*, vol. 80, (Jul.-83) pp. 4045-4049.
Bischoff, et al., *Analytical Biochemistry*, vol. 164 (1987) pp. 336-344.

*Primary Examiner*—Jill A. Johnston
*Attorney, Agent, or Firm*—Donna R. Fugit

[57] ABSTRACT

An assay device includes a filter stack in an enclosure having a base portion and a lid. The filter stack has a hydrophilic membrane having a binder for an analyte thereon, a hydrophobic membrane under the hydrophilic membrane and a pad of absorbent material under the hydrophobic membrane. The lid includes an upwardly extending rim which defines a recess having an insert therein. Aligned openings in the lid and insert provide access to the hydrophilic membrane. The hydrophobic membrane is impervious to the passage of an aqueous liquid until wetted by a wetting agent. The invention includes a kit of materials for performing an assay for an analyte which includes the device.

20 Claims, 2 Drawing Sheets

TEST DEVICE INCLUDING FLOW CONTROL MEANS

This application is a continuation of application Ser. No. 07/410,372, filed Sep. 21, 1989, and now abandoned.

BACKGROUND OF THE INVENTION

1. Field of the Invention

This invention relates to assay for an analyte, and more particularly relates to membrane flow-through assay and a device useful therein.

2. Background of the Invention

Assay systems which are both rapid and sensitive have been developed to determine the concentration of a substance, generally referred to as the analyte, present in low concentration in a fluid sample. Immunoassays depend on the binding of an antigen or hapten to a specific antibody and have been particularly useful because they give high levels of specificity and sensitivity. These assays employ one of the above reagents in labeled form, the labeled reagent being referred to as the tracer.

Enzymes have often been used as labels in immunoassay. In conventional enzyme immunoassay (EIA), an enzyme is covalently conjugated with one component of a specifically binding antigen antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

A convenient format for EIA is solid phase immunoassay in which one of the assay reagents is immobilized on a solid support. The solid support may be in the form of a dipstick, the inside wall of a test tube or cuvette or the well of a microtiter plate. A particularly useful solid support is a microporous membrane.

Membrane assay is often referred to as flow through assay since the assay steps are performed sequentially with the fluid phase of each step passing through the membrane before the next step is initiated. An assay device in which fluid flow is gravity controlled is disclosed in U.S. Pat. No. 4,111,754 to Park. Flow-through assay devices in which flow is enhanced by capillary action induced by an absorbent pad in contact with the membrane are disclosed by U.S. Pat. No. 3,888,629 to Bagshaw and U.S. Pat. No. 4,632,901 to Valkirs et al. A dipstick assay device using flow-through is disclosed by Tom et al. in U.S. Pat. No. 4,366,241. In the Bagshaw, Valkirs et al. and Tom et al. devices, fluid flow through the membrane cannot be controlled by the technician. Cole et al., in U.S. Pat. No 4,246,339 discloses a device in which capillary action is controlled by biasing the absorbent pad into and out of contact with the membrane. Devices in which flow is initiated by vacuum are described in U.S. Pat. No. 4,277,560 to Gray and U.S. Pat. No. 4,812,293 to McLaurin et al.

While the devices disclosed in the above patents using mechanical means to promote flow have advanced the art of flow through assay, there remains a need for a device in which flowing can be controlled merely by passing a flow controlling reagent through the membrane. It is toward fulfillment of this need that the present invention is directed.

SUMMARY OF THE INVENTION

An assay device includes a filter stack inside of an enclosure having a base portion and a lid. The filter stack comprises a porous hydrophilic membrane which preferably has thereon a binder for an analyte. The hydrophilic membrane is positioned over a porous hydrophobic membrane which is impervious to the passage of an aqueous liquid until activated by a wetting agent. The hydrophobic membrane is positioned over an absorbent pad. An opening in the lid provides access to the hydrophilic membrane.

In a preferred device, the lid has an upwardly projecting rim which defines a recess having an insert therein wherein the recess has an opening in alignment with the opening in the lid. The most preferred device includes a spacing layer between the hydrophobic membrane and the absorbent pad to prevent liquids from backing up into the hydrophilic membrane.

The invention includes a kit of materials useful in performing an assay for an analyte which includes the device of the invention. The kit may also include other components of a conventional immunoassay such as a tracer comprising a label conjugated to the analyte or an antianalyte. If the label is an enzyme, the kit may include a substrate for the enzyme.

Thus, an assay device useful in a flow-through assay for an analyte includes structure to generate flow of assay fluids through a membrane by capillary action and structure to prevent flow until deemed appropriate. The device of the invention is particularly well suited to immunoassay of an analyte in which an antigen-antibody binding reaction is slow and liquid flow must be prevented until binding is complete. Since the means to prevent flow is a simple hydrophobic membrane, many of which are commercially available, and the means to initiate flow at a desired time is a simple readily available chemical reagent, no complex mechanical apparatus is required. The device is accordingly simple and inexpensive to manufacture, facile to use, and admirably suited for use in a physician's office, by laboratory personnel of limited training, or even in the home.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

Figure 1:
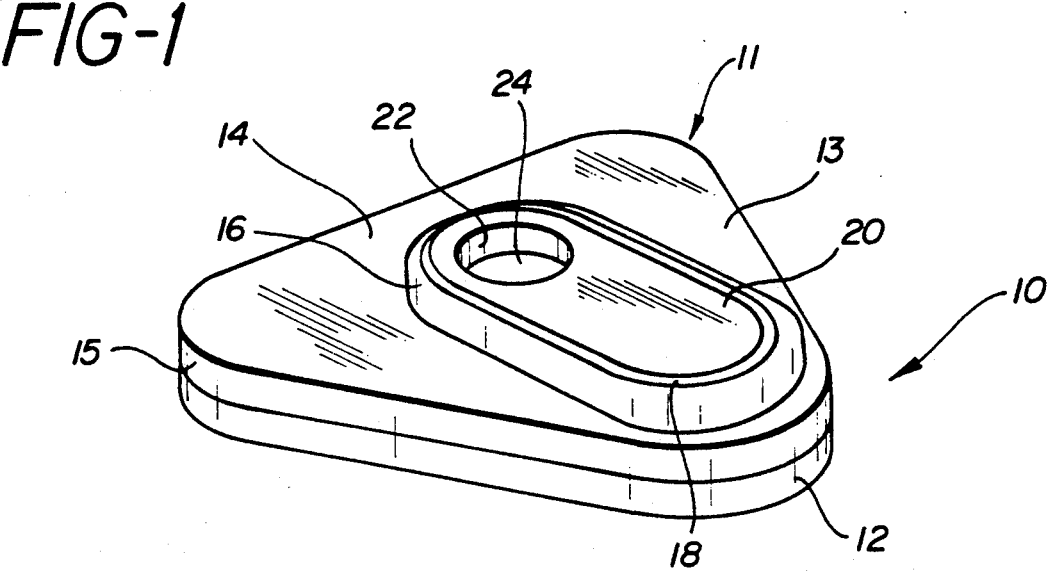
FIG. 1 is a perspective view of the preferred assay device of the invention.

The assay device of the invention will first be described by reference to the figures. FIG. 1 illustrates device 10 including an enclosure 11 having a base portion 12 and a lid portion 13. Lid 13 includes a top wall 14 and a substantially vertical side wall 15. A rim 16 projects upwardly from top wall 14. Rim 16 defines a recess 18 having therein a preferably colored insert 20 having an opening 22 in alignment with an opening 24 in lid 14.

Figure 2:
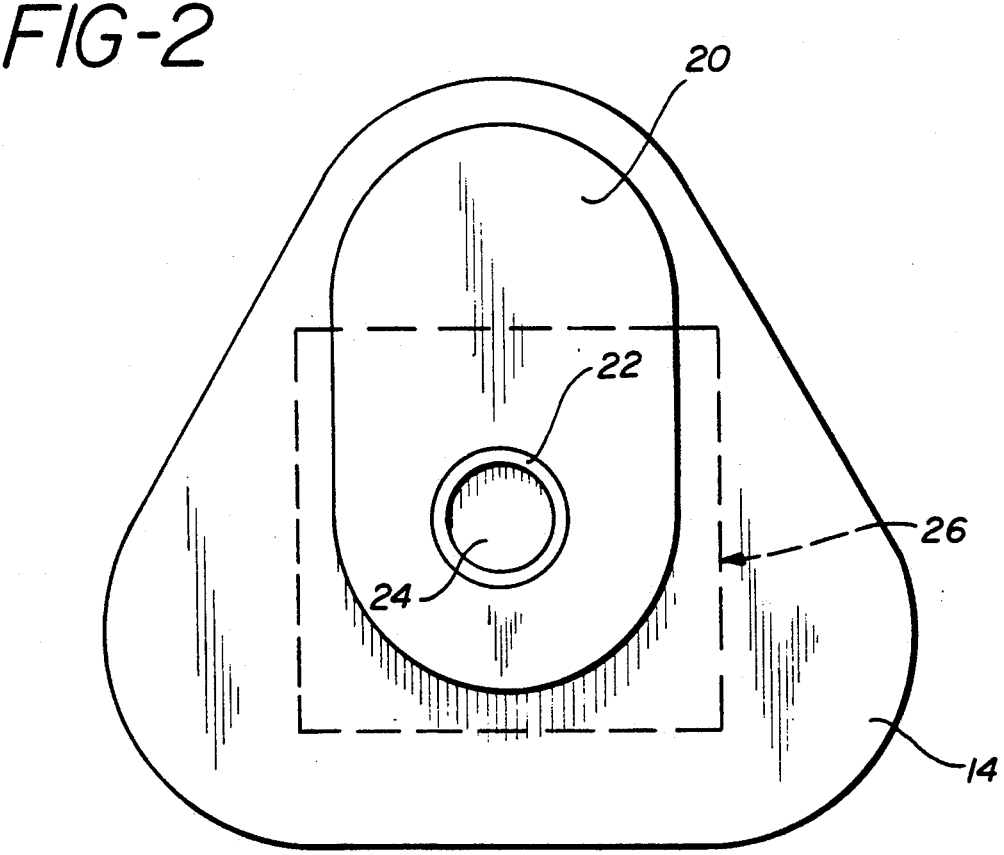
FIG. 2 is a top perspective view of the assay device of the invention showing the filter stack in phantom.

FIG. 2 shows a filter stack 26 in phantom positioned under openings 22 and 24 respectively.

Figure 3:
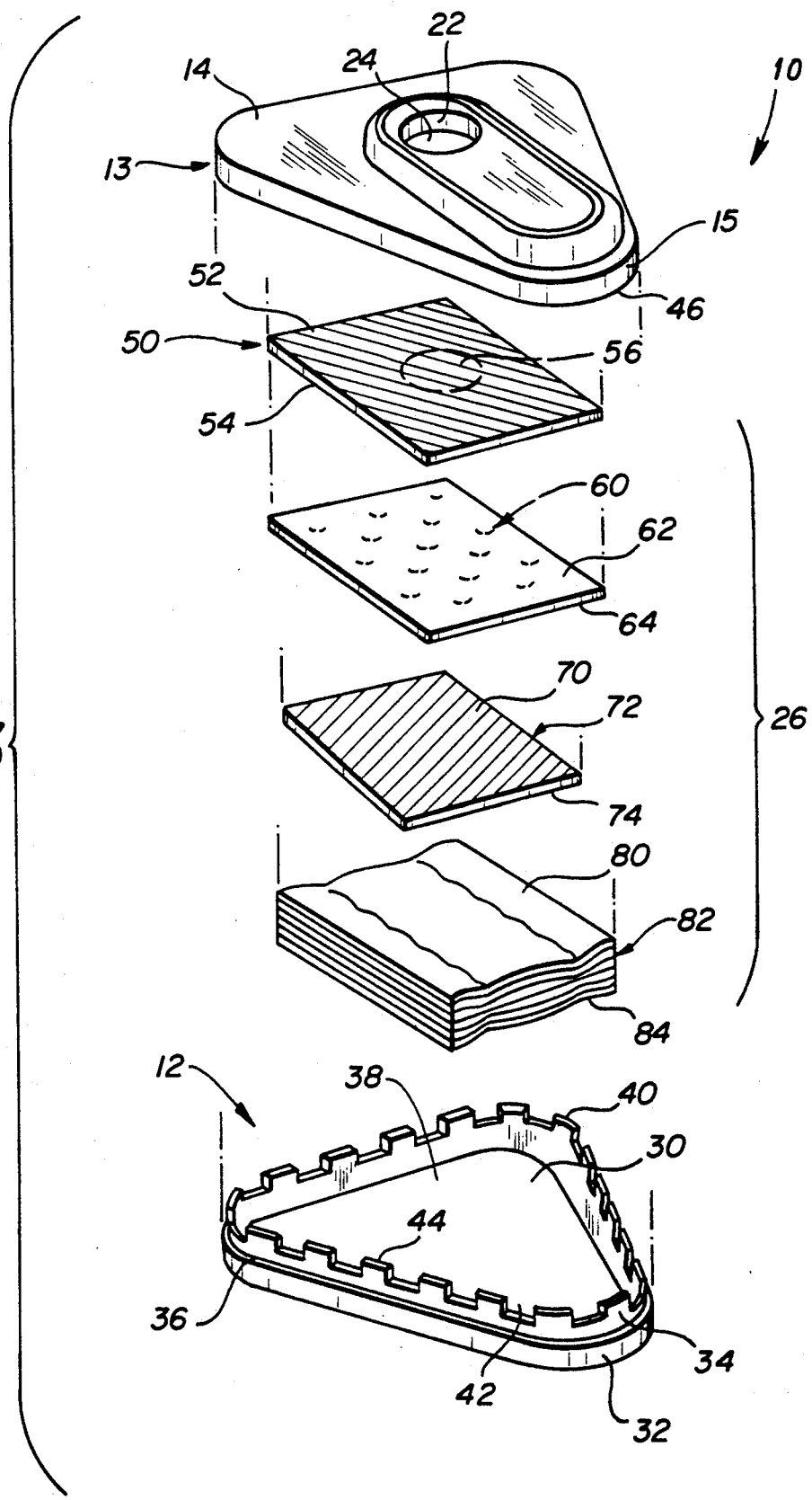
FIG. 3 is an exploded perspective view of the preferred assay device of the invention showing the arrangement of the components of the device.

Details of base portion 12 and filter stack 26 are more clearly illustrated in FIG. 3. Base portion 12 has a bottom wall 30 and a substantially vertical side wall separated into lower section 32 and upper section 34 by a substantially horizontal shelf 36. Bottom wall 30 and side wall sections 34 and 36 together define a chamber 38 which receives filter stack 26.

Upper section 34 has a plurality of projections 40 extending upwardly therefrom. Projections 40 are separated from each other by spaces 42. When the device is assembled as shown in FIG. 1, top wall 14 of lid 13 rests on upper surfaces 44 of projections 40 so that the lower edge 46 of side wall 15 is preferably positioned slightly above horizontal shelf 36 thereby providing air communication from the external environment to chamber 38 through spaces 42.

Filter stack 26 includes a porous hydrophilic membrane 50 having an upper surface 52 and a lower surface 54. Upper surface 52 preferably includes a test area 56 coated with a binder as described below.

While FIG. 3 illustrates test area 56 to be a restricted area of membrane 50, it is understood that the test area merely represents that portion of membrane 50 to which a binding reagent is conveniently and economically attached. If desired, the entire membrane 50 or any portion thereof may be coated with the binder. In general, the test area has a surface area such that it is capable of supporting binder in a concentration of at least 1, preferably 10 and most preferably at least 40 $\mu g/cm^2$.

Test area 56 is positioned below openings 22 and 24 of insert 20 and lid 14, respectively. The bottom surface 54 of hydrophilic membrane 50 is positioned to contact a porous hydrophobic membrane 60 having an upper surface 62 and a bottom surface 64. Bottom surface 64 of membrane 60 preferably rests on the upper surface 70 of an optional porous spacing layer 72 preferably of porous material. The bottom surface 74 of spacing layer 72 rests on the upper surface 80 of a pad 82 of absorbent material, the bottom surface 84 of which rests on bottom wall 30 of base portion 12. While FIG. 3 shows pad 82 preferably to include a plurality of members, it is evident that a single pad of appropriate thickness may be used. Alternatively, the plurality of members may be sewn together or attached by any other convenient means, or membranes 50, 60 and 72 and pad 82 may all be sewn or bound together to give a unitary filter stack.

Insert 20 and base portion 12 and lid 13 of enclosure 11 may preferably be made of any plastic material such as polyethylene, polystyrene or most preferably polypropylene. Insert 20 may be of any color, preferably a color which contrasts with the color which develops on test area 56 resulting from a positive assay. It is understood that the device may be of any shape and is not limited to the triangular shape shown in the drawings.

Hydrophilic membrane 50 may be of any material which wets readily with an aqueous assay solution, preferably a material which is suitable for attachment of an assay binding reagent, such as a capture antibody. Suitable membranes are, for example, glass, nylon and, preferably cellulose. The most preferred membrane is a nitrocellulose membrane having a pore size of about 2 to 12 $\mu$, preferably about 3 to 5 $\mu$. Suitable hydrophilic membranes are commercially available from Pall Corp., East Hills, N.Y., under the trade name IMMUNODYNE ™.

Hydrophobic membrane 60 may be positioned immediately below hydrophilic membrane 50 in filter stack 26. In accordance with the invention, the hydrophobic membrane is impervious to the passage of an aqueous assay fluid until activated by a wetting agent. Thus, suitable hydrophobic membranes are, for example, porous polysiloxane, polyethylene and polytetrafluoroethylene membranes. Glass fiber membranes coated with polyethylene and available from Pall may be used. Preferred hydrophobic membranes are glass fiber membranes coated with perfluoroalkylsilanes such as 1H, 1H,2H,2H-perfluorooctyltriethoxysilane, perfluorooctadecylsiloxane and trichlorooctadecylsilane. A typical procedure for coating glass fiber membranes with perfluoroalkylsilanes is given in Example I.

Porous spacing layer 72 may be formed for example from a non woven cellulose, such as rayon, and generally has a pore size greater than that of hydrophobic membrane 60. The spacing layer primarily functions to prevent liquids which have passed through the upper layers and been absorbed in pad 80, as described below, from backing up into the wetted hydrophobic layer and ultimately into the test area. It is understood, however, that the spacing layer, while preferred, may be eliminated in those cases where the characteristics of the remaining layers are such that the risk of material backing up into the test area is substantially nil. Suitable rayon sheets are commercially available from Schleicher and Schuell, Keene, N.H.

Absorbent pad 82 consists of a porous material having an absorbing capacity sufficient to absorb substantially all the liquids of the assay reagents and any wash solutions. Pad 82 also serves to initiate the capillary action which draws the assay liquids through the test area and as such may preferably be formed from a cellulose material, as, for example, absorbent cellulose paper. Suitable absorbent cellulose paper is available from Filtration Sciences, Mount Holly Springs, Pa.

The assay device of the invention is contemplated to be used in any flow through immunoassay procedure including competitive and preferably sandwich assays. As mentioned above, the hydrophilic membrane may be coated with a binder for an analyte. If the analyte is an antigen, the binder to be coated onto the hydrophilic membrane is generally a specific antibody, often termed a capture antibody. If the analyte is an antibody, the binder may be a specific antigen, often termed a capture antigen. In either case, after the coating of binder is applied to the hydrophilic membrane, it is preferred to fill any unoccupied binding sites with an inert protein to prevent nonspecific binding of any other assay reagent, such as the tracer, to the membrane. (In the present disclosure, the term inert protein means a protein which is immunologically unreactive toward any other component of the assay and which does not substantially bind nonspecifically to other proteins in the assay medium, with the understanding that the inert protein may well be immunologically reactive toward other materials which are not part of the assay of the invention.) Representative nonlimiting examples of suitable inert proteins are albumin and casein.

In another embodiment of flow through assay which may advantageously be performed on the device of the invention, the hydrophilic membrane may be coated with the inert protein. In this assay embodiment, analyte affixes directly to the coating of inert protein. Need for capture antibody or antigen is thus eliminated.

It is appreciated that, for immunoassay, the invention contemplates providing the device with the inert protein and/or binder firmly affixed to the hydrophilic membrane, or preferably to the test area of the hydrophilic membrane, with the other elements of the filter stack assembled in the enclosure. It is understood, however, that for some applications, it may be desirable to omit the binder and provide a bare hydrophilic membrane.

Performance of an assay using the assembled device is initiated by adding an aqueous solution suspected of containing analyte to the coated hydrophilic membrane through the apertures 22 and 24. The aqueous solution wets the hydrophilic membrane and binding of analyte to binder takes place. Flow of the assay solution, however, does not take place because the aqueous solution does not wet the hydrophobic membrane placed under the hydrophilic membrane in the filter stack. Accordingly, as much time as necessary to complete binding may be allowed to pass, in contrast to prior art devices wherein flow is not under control of the technician.

When binding is complete, flow may be initiated by adding a modifying reagent through apertures 22 and 24 which wets the hydrophobic membrane. Suitable wetting agents are for example, acetone, surfactants and detergents. Preferred wetting agents are alcohols, most preferably methanol.

In accordance with the invention, it has been found that the hydrophobic membrane, once wetted by the wetting agent, remains permeable to subsequent aqueous reagents used in the assay. Thus, the hydrophilic membrane having analyte captured thereon may thereafter by treated sequentially with the tracer solution and a color forming reagent solution and any appropriate wash solutions in accordance with conventional immunoassay procedures.

As is well known in the immunoassay art, the tracer in a sandwich assay may be an antibody specific for the analyte having a label covalently conjugated thereto. In a competitive assay, the tracer includes the label conjugated to the analyte, and the tracer and analyte compete for binding sites on the binder. Suitable labels are, for example, absorbing dyes, fluorescent dyes and preferably enzymes.

In the preferred assay using an enzyme as the label, a solution of a color forming reagent, such as a chromogen is passed through the test area after binding of the tracer. Enzyme captured on the test area as part of the tracer reacts with the chromogen to form a colored product which preferably precipitates on the membrane and may readily be observed against the background of different color of insert 20. It is evident that if the label is an absorbing dye, the color forming reagent is not needed. If the label is a fluorescent dye, detection is performed by applying excitation light to the test area and observing for fluorescence.

It is understood that immunoassay for an analyte as described above is only one application contemplated for the device of the invention. One skilled in the art will immediately recognize that the device may be used in an assay wherein the analyte is a specific sequence in a sample of DNA or RNA. For example, a sample of DNA may be denatured by a conventional method, such as heating, and the denatured material absorbed onto the hydrophilic membrane. Absorption may be either covalent using crosslinkers well-known in the art (Bischoff et al., *Anal. Biochem.*, 1987, 164, 336) or non-covalent (Ward et al., *Proc. Nat'l Acad. Sci. U.S.A.*, 1983, 80, 4045). After activation of the hydrophobic membrane by treatment with the wetting agent, a solution containing a labeled strand complementary to the analyte sequence may be passed through. If hybridization takes place, the label will be captured on the hydrophilic membrane and its detection is then diagnostic for the analyte sequence.

In accordance with a further aspect of the invention, there is provided a reagent kit for performing an assay for an analyte which includes the enclosure having the filter stack therein. The hydrophilic membrane of the filter stack may have a binder for the analyte affixed thereto, preferably to a test area of the hydrophilic membrane. The kit may include a tracer and a chromogen, preferably supplied as aqueous solutions, and a wetting agent. Standards (samples having known concentrations of analyte), buffers, and wash solutions may be included in the kit and be supplied in suitable containers, as test vials.

EXAMPLE I

Coating Procedure with Perfluoroalkylsilanes

Glass fiber filters (Gelman type A1E, 6 g) were cut into quarters and refluxed in 200 ml of toluene for 2 hours while toluene water was collected in a Dean Stark trap. 1H,1H,2H,2H-perfluorooctyltriethoxysilane (10 g, 19.6 mmoles) was added and reflux continued for 4 hours with periodic removal of toluene water from the Dean Stark trap. After cooling, the filter was washed with toluene and dried, finally overnight in an oven at 120° C.

EXAMPLE II

The perfluoroalkylsilane coated membrane of Example I was placed in the device illustrated in the figures with a porous hydrophilic nitrocellulose membrane (Pall Corp.) on top of the filter stack. Phosphate buffer (100 $\mu$L) was added through the openings in the insert and lid and the hydrophilic membrane immediately became wet. No flow was observed for 5 minutes. Methanol (300 $\mu$L) was added, whereupon flow of the solution through the membranes and into the absorbent pad occurred.

In a control experiment using an uncoated glass fiber filter, the phosphate buffer flowed through the filter stack without methanol addition.

Thus, the invention provides a flow through assay device giving the user control over initiation of flow by a simple reagent addition instead of by a mechanical change.

What is claimed is:

1. A device for assay of an analyte comprising an enclosure and a filter stack therein, said filter stack comprising:
   a) a porous hydrophilic membrane having a first surface and a second surface, said hydrophilic membrane having thereon a binder for an analyte;
   b) a porous hydrophobic membrane having a first surface and a second surface, said first surface being in contact with said second surface of said hydrophilic membrane, said hydrophobic membrane being impermeable to an aqueous fluid and permeable to a solution of a wetting agent and an aqueous fluid; and c) an absorbent material in contact with said second surface of said hydrophobic membrane such that said hydrophilic membrane, said hydrophobic membrane and said absorbent material are in fluid communication when said hydrophobic membrane is permeable.

said enclosure including an opening providing access to the first surface of said hydrophilic membrane.

2. The device of claim 1 wherein said porous hydrophilic membrane comprises a material selected from the group consisting of glass, nylon and cellulose.

3. The device of claim 1 wherein said binder is selected from the group consisting of an antibody, an antigen and an inert protein.

4. The device of claim 3 wherein said binder is an inert protein and said inert protein is selected from the group consisting of albumin and casein.

5. The device of claim 1 wherein and porous hydrophobic membrane comprises a material selected from the group consisting of polyethylene, polysiloxane, polytetrafluoroethylene and glass fiber coated with a hydrophobic material.

6. The device of claim 5 wherein said hydrophobic membrane material is glass fiber coated with a hydrophobic material and said hydrophobic material is selected from the group consisting of polyethylene and a perfluoroalkylsilane.

7. The device of claim 1 wherein said absorbent material is cellulose.

8. The device of claim 7 wherein said cellulose is absorbent cellulose paper.

9. A device for assay of an analyte comprising an enclosure and a filter stack therein, said filter stack comprising:
a) a porous hydrophilic membrane;
b) a porous hydrophobic membrane in contact with said hydrophilic membrane, said hydrophobic membrane being impermeable to an aqueous fluid and permeable to a solution of a wetting agent and an aqueous fluid; and
c) absorbent material in contact with said hydrophobic membrane such that said hydrophobic membrane and said absorbent material are in fluid communication when said hydrophobic membrane is permeable.

said enclosure having an opening providing access to said hydrophilic membrane.

10. The device of claim 9 wherein said enclosure includes a base portion and a lid, said lid having an upwardly projecting rim which defines a recess including said opening.

11. The device of claim 10 wherein said recess has an insert therein, said insert including an opening aligned with said opening in said lid.

12. The device of claim 9 further comprising a binder on said hydrophilic membrane.

13. A device for assay of an analyte comprising an enclosure and a filter stack therein, said filter stack comprising:
a) a porous hydrophilic membrane having a top surface and a bottom surface and a binder for an analyte affixed to a test area thereof;
b) a porous hydrophobic membrane having upper and lower surfaces, said upper surface being in contact with the bottom surface of said hydrophilic membrane, said hydrophobic membrane being impermeable to an aqueous fluid and permeable to a solution of a wetting agent and an aqueous fluid;
c) a spacing layer of porous material having top and bottom surfaces, said top surface being in contact with said lower surface of said hydrophobic membrane;
d) an absorbent material in contact with said bottom surface of said spacing layer such that said hydrophilic membrane, hydrophobic membrane, spacing layer and absorbent material are in fluid communication when said hydrophobic membrane is permeable, said enclosure comprising a base portion and a lid, said lid having an upwardly extending rim defining a recess, said recess having an insert therein, said lid and insert having aligned openings positioned over and providing access to said test area of said hydrophilic membrane.

14. The device of claim 13 wherein said porous spacing layer material is cellulose.

15. The device of claim 13 wherein said insert is colored.

16. A kit of materials for performing an assay for an analyte comprising:
a) an enclosure;
b) a filter stack in said enclosure, said filter stack comprising a porous hydrophilic membrane having a binder for an analyte thereon, a hydrophobic membrane in contact with said hydrophilic membrane and an absorbent material in contact with said hydrophobic membrane, said hydrophobic membrane being impermeable to an aqueous fluid and permeable to a solution of a wetting agent and an aqueous fluid; and
c) a tracer including a label conjugated to one of said analyte and an antianalyte.

17. The kit of claim 16 wherein said label is an enzyme and said kit further comprises a chromogen reactive with said enzyme to give a colored product.

18. The kit of claim 16 wherein said binder is selected from the group consisting of an antibody, an antigen and an inert protein.

19. The kit of claim 16 further comprising a wetting agent capable of permeabilizing said hydrophobic membrane to passage of aqueous fluids.

20. The kit of claim 16 further comprising a reagent selected from the group consisting of a known quantity of said analyte, a buffer and a wash solution.

* * * * *